US006653502B2

(12) United States Patent
Geissler

(10) Patent No.: US 6,653,502 B2
(45) Date of Patent: Nov. 25, 2003

(54) PROCESS FOR PREPARING PHENYLACETIC ACID DERIVATIVES

(75) Inventor: Holger Geissler, Mainz (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/037,078

(22) Filed: Nov. 9, 2001

(65) Prior Publication Data

US 2002/0062041 A1 May 23, 2002

(30) Foreign Application Priority Data

Nov. 18, 2000 (DE) .......................... 100 57 262

(51) Int. Cl.[7] .......................... C07C 67/36; C07C 51/12
(52) U.S. Cl. .......................... 560/97; 562/406
(58) Field of Search .......................... 560/97; 562/406

(56) References Cited

U.S. PATENT DOCUMENTS

| | | | |
|---|---|---|---|
| 2,730,546 A | * | 1/1956 | Reppe et al. |
| 3,988,358 A | * | 10/1976 | Heck |
| 4,034,004 A | * | 7/1977 | Cassar et al. |
| 5,003,104 A | * | 3/1991 | Paulik et al. |
| 5,315,029 A | * | 5/1994 | Chockalingam |

FOREIGN PATENT DOCUMENTS

| | | |
|---|---|---|
| DE | 1 914 391 | 11/1969 |
| DE | 25 21 610 | 9/1976 |
| EP | 0 338 852 | 10/1989 |
| GB | 1 245 029 | 9/1971 |
| GB | 1 537 862 | 1/1979 |

OTHER PUBLICATIONS

Thompson and Twigg " Carbonylation, Direct Synthesis of Carbonyl Compounds" Plenum Press, New York, 1991, pp. 91–97 & 111–119.
EPO Search Report for application No. 01126255, mail date Mar. 26, 2002.
H. Urata, et al., "Transition metal complex catalyzed carbonylation of organic halides in N,N,N'N'–Tetraalkylurea solution in the absence of added base", J. Org. Chem., 1991, 56, pp. 4320–4322.
H. Urata, et al., "Transition metal complex catalyzed carbonylation of organic halides in the presence of molecular sieves instead of base", Tetrahedron Letters, 1991, vol. 32, No. 36, pp. 4733–4736.

* cited by examiner

*Primary Examiner*—Samuel Barts
*Assistant Examiner*—Paul A. Zucker
(74) *Attorney, Agent, or Firm*—Scott E. Hanf

(57) ABSTRACT

A process for preparing phenylacetic acid derivatives of the formula (I) by reacting benzyl chlorides of the formula (II)

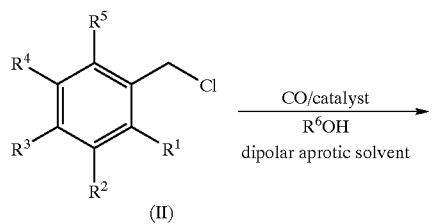

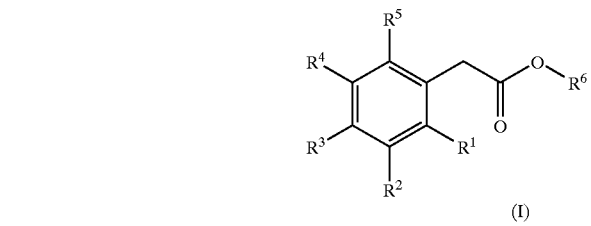

with a compound of the formula $R^6OH$ and with carbon monoxide in a dipolar aprotic solvent in the presence of a catalyst which comprises at least one compound of a transition metal of subgroup VIII of the Periodic Table of the Elements, where $R^1$, $R^2$, $R^3$, $R^4$, and $R^5$ independently of one another are the following radicals:
a hydrogen or fluorine atom;
a $CH_2Cl$ radical;
a $HO_2CCH=CH-$, $NC-$ or $CF_3-$ group;
an alkyl, alkoxy or acyloxy radical having in each case 1 to 18 carbon atoms; or
a $C_6-C_{18}$-aryloxy, aryl or heteroaryl radical.

16 Claims, No Drawings

PROCESS FOR PREPARING PHENYLACETIC ACID DERIVATIVES

BACKGROUND OF THE INVENTION

The present patent application describes a process for preparing substituted phenylacetic acids or their esters by reacting substituted benzyl chlorides with carbon monoxide and alcohols or water in the presence of a catalyst and a dipolar aprotic solvent.

Substituted phenylacetic acids and their esters are important intermediates in the pharmaceutical industry and the agrochemical industry.

The synthesis of phenylacetic acids, starting from benzyl chlorides, and the synthesis of phenylacetic esters is described by Colquhoun, Thompson and Twigg ("Carbonylation, Direct Synthesis of Carbonyl Compounds" Plenum Press, New York, 1991, pages 91–97 and 111–119). The reactions of benzyl chlorides with carbon monoxide and water or an alcohol proceed successfully according to this report in the presence of catalytic amounts of compounds of nickel, cobalt, iron, ruthenium, rhodium, or palladium, and with the addition of stoichiometric amounts of a base in order to neutralize the hydrogen halide produced in the reaction.

SUMMARY OF THE INVENTION

Owing to the disadvantages of the known processes and the increasing requirement, the object was to find a process which enables substituted or unsubstituted benzyl chlorides to be converted in a simple and economic manner and in high yields to give the corresponding phenylacetic acid derivatives.

DETAILED DESCRIPTION OF THE INVENTION

This object is achieved by a process for preparing phenylacetic acid derivatives of the formula (I) by reacting benzyl chlorides of the formula (II)

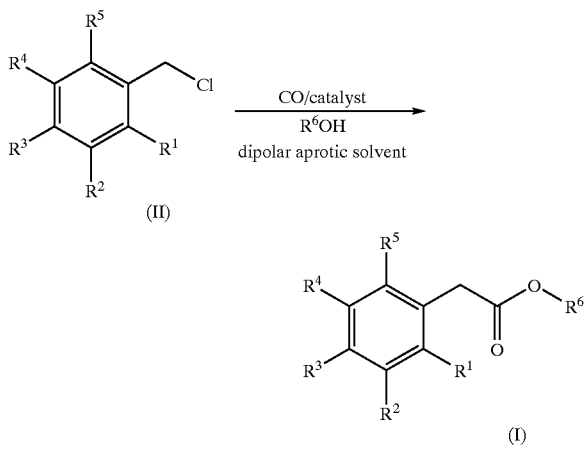

with a compound of the formula $R^6OH$ and with carbon monoxide in a dipolar aprotic solvent in the presence of a catalyst which comprises at least one compound of a transition metal of subgroup VIII of the Periodic Table of the Elements, where $R^1$, $R^2$, $R^3$, $R^4$, and $R^5$ independently of one another are the following radicals:

a hydrogen or fluorine atom;
a $CH_2Cl$ radical;
a $HO_2CCH=CH-$, $NC-$ or $CF_3-$ group;
an alkyl, alkoxy or acyloxy radical having in each case 1 to 18 carbon atoms; or
a $C_6-C_{18}$-aryloxy, aryl or heteroaryl radical, where, as heteroatoms, 1 to 3 atoms selected from the group consisting of O, N and/or S are present;
a $R^8{}_2P(=O)-$, $R^9C(=O)-$, $R^9OC(=O)-$, $R^9OC(=O)CH=CH-$, $R^{10}C(=O)-$,
$R^{10}OC(=O)-$, $R^{10}OC(=O)CH=CH-$, or $R^{10}{}_2P(=O)-$ radical, where $R^8$ is a $C_1-C_4$-alkyl radical, $R^9$ is a $C_1-C_{18}$-alkyl radical or hydrogen and $R^{10}$ is a $C_6-C_{18}$-aryl radical;
or where at least two of the radicals $R^1$, $R^2$, $R^3$, $R^4$, and $R^5$ are linked to one another and form at least one aliphatic or aromatic ring having 5 to 18 carbon atoms.
$R^6$ is hydrogen, a $C_1-C_{18}$-alkyl radical, in particular a $C_1-C_4$-alkyl radical, or a $C_6-C_{18}$-aryl radical.

The radicals $R^1$, $R^2$, $R^3$, $R^4$, and $R^5$ are, in particular, independently of one another hydrogen, fluorine, $C_1-C_8$-alkyl, or $C_1-C_8$-alkoxy, or two of the radicals $R^1$, $R^2$, $R^3$, $R^4$, and $R^5$ are linked to one another and preferably form an aliphatic or aromatic ring having 5 to 10 carbon atoms. Preferably, the radicals $R^1$, $R^2$, $R^3$, $R^4$ and $R^5$ independently of one another are hydrogen, fluorine and $C_1-C_4$-alkyl.

The inventive process can be carried out in the presence or absence of an ionic halide.

Usually, the ionic halide is an alkali metal halide, ammonium halide, alkylammonium halide or phosphonium halide, in particular an alkali metal halide or ammonium halide, where halide has the meaning chloride, bromide or iodide, in particular chloride or bromide, preferably chloride.

The ionic halide used can be ammonium bromide, lithium bromide, sodium bromide, potassium bromide, tetrabutylphosphonium bromide, ammonium chloride, dimethylammonium chloride, diethanolammonium chloride, lithium chloride, sodium chloride, potassium chloride, tetrabutylphosphonium chloride, ammonium iodide, lithium iodide, sodium iodide, potassium iodide and/or tetrabutylphosphonium iodide, in particular lithium chloride, ammonium chloride, dimethylammonium chloride, and/or diethanolammonium chloride.

In the case of the inventive process, however, the presence of the ionic halide can also be dispensed with and the process can be carried out in the absence of the ionic halide.

In a particular embodiment of the process, the ionic halide can be used in particular when the catalyst comprises palladium.

The catalyst comprises at least one transition metal compound of subgroup VIII, in particular compounds of palladium, nickel and/or cobalt, preferably compounds of palladium and/or cobalt, particularly preferably palladium compounds.

For the inventive process, a palladium catalyst that contains nickel, cobalt or palladium applied to a support material can also be used. A supported catalyst of this type has the advantage that it may be removed from the reaction mixture in a simple manner, for example by filtration.

When palladium catalysts are used, it has proven useful in a number of cases for the palladium catalyst to comprise at least one palladium(II) compound, in particular $PdCl_2$, $PdBr_2$ or $Pd(OAc)_2$, preferably $PdCl_2$, or at least one palladium(0) compound, in particular $Pd_2dba_3$, where dba is dibenzylideneacetone, $Pd(P(C_6H_5)_3)_4$ or $Pd(C_8H_{12})_2$, preferably $Pd_2dba_3$.

In a number of cases it has also proved to be expedient that the catalyst additionally contains a ligand, in particular a phosphine compound.

Phosphine compounds coming into consideration, are, for example, a monophosphine, in particular a tri-($C_1$–$C_6$)-alkylphosphine or a triarylphosphine, or a diphosphine. Triphenylphosphine, tritolylphosphine, bis(diphenylphosphino)ethane, 1,3-bis(diphenylphosphino)propane or 1,4-bis(diphenylphosphino)butane, in particular triphenylphosphine can be used very successfully.

According to a particular embodiment, the palladium catalyst contains a bis(triphenylphosphine)palladium(II) compound, for example bis(triphenylphosphine)palladium(II) chloride or bis(triphenylphosphine)palladium(II) bromide.

The catalyst is usually used in an amount of 0.00001 to 0.3 mol of transition metal, in particular 0.0001 to 0.2 mol of transition metal, preferably 0.0005 to 0.1 mol of transition metal, per mole of benzyl chloride of the formula (II).

In a multiplicity of cases it is sufficient to carry out the reaction at a CO pressure of 0.5 to 20 MPa, in particular 0.8 to 10, preferably 1.0 to 6 MPa.

Usually, the reaction can be carried out very successfully at a temperature of 20 to 220° C., in particular 40 to 200° C., preferably 60 to 180° C.

Suitable dipolar aprotic solvents are dioxane, tetrahydrofuran, N-($C_1$–$C_{18}$-alkyl)pyrrolidone, ethylene glycol dimethyl ether, $C_1$–$C_4$-alkylesters of aliphatic $C_1$–$C_6$-carboxylic acids, $C_1$–$C_6$-dialkyl ethers, N,N-di-($C_1$–$C_4$-alkyl)amides of aliphatic $C_1$–$C_4$-carboxylic acids, sulfolane, 1,3-di-($C_1$–$C_8$-alkyl)-2-imidazolidinone, N-($C_1$–$C_8$-alkyl)caprolactam, N,N,N', N'-tetra-($C_1$–$C_8$-alkyl)urea, 1,3-di-($C_1$–$C_8$-alkyl)-3,4,5,6-tetrahydro-2(1H)-pyrimidone, N,N,N',N'-tetra-($C_1$–$C_8$-alkyl)sulfamide, 4-formylmorpholine, 1-formylpiperidine or 1-formylpyrrolidine, in particular N-($C_1$–$C_{18}$-alkyl)pyrrolidone, N,N-di-($C_1$–$C_4$-alkyl)amide of aliphatic $C_1$–$C_4$-carboxylic acids, 4-formylmorpholine, 1-formylpiperidine or 1-formylpyrrolidine, preferably N-methylpyrrolidone, N-octylpyrrolidone, N-dodecylpyrrolidone, N,N-dimethylformamide, N,N-dimethylacetamide, 4-formylmorpholine, 1-formylpiperidine or 1-formylpyrrolidine, particularly preferably N-methylpyrrolidone, N,N-dimethylformamide or N,N-dimethylacetamide. Mixtures of the abovementioned dipolar aprotic solvents may also be used.

In the very particularly preferred variant, N-methylpyrrolidone is used as solvent.

When N-methylpyrrolidone is used as solvent, the resulting hydrogen chloride can be isolated as aqueous hydrogen chloride following the reaction and the solvent N-methylpyrrolidone can be reused.

The compound of the formula $R^6OH$, corresponding to an alkyl alcohol or water, can be added in an amount of 0.1 to 50 mol in each case per mole of benzyl chloride of the formula (II). Usually, the reaction is carried out with an amount of alkyl alcohol or water equivalent to 0.2 to 10, in particular 0.5 to 4, preferably 1 to 4, mol per mole of benzyl chloride of the formula (II).

With the use of benzyl chlorides of the formula (II) where at least one of the radicals $R^1$, $R^2$, $R^3$, $R^4$, and $R^5$ independently of one another is a $CH_2Cl$ radical, corresponding to the inventive process, phenylacetic acids of the formula (I) are obtained in which at least one of the radicals $R^1$, $R^2$, $R^3$, $R^4$, and $R^5$ independently of one another is a $CH_2Cl$ radical. These products are, in accordance with the described process, again benzyl chlorides of the formula (II) and are reacted further in accordance with the described process.

Therefore, one mole of benzyl chloride of the formula (II) where at least one of the radicals $R^1$, $R^2$, $R^3$, $R^4$ and $R^5$ independently of one another is a $CH_2Cl$ radical, is equivalent to many moles of benzyl chloride, corresponding to the number of $CH_2Cl$ groups.

With the use of benzyl chlorides of the formula (II) where at least one of the radicals $R^1$, $R^2$, $R^3$, $R^4$, and $R^5$ independently of one another is a $CH_2Cl$ radical and where at least two $CH_2Cl$ groups are in the ortho position, in addition to the phenylacetic acids of the formula (I), 3-isochromanone derivatives of the formula (III) are obtained.

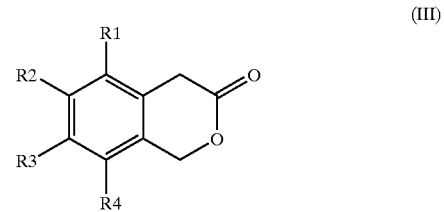

According to a particular embodiment of the inventive process, the benzyl chloride of the formula (II), the catalyst, the dipolar aprotic solvent and if appropriate also the compound $R^6OH$ and if appropriate the ionic halide are charged, the CO pressure and temperature are set and then the alkyl alcohol or the water or a mixture consisting of the alkyl alcohol or water and the diprotic solvent is added.

During the reaction intensive mixing of the reaction partners is provided, in order to ensure a rapid reaction course.

The inventive process is suitable both for continuous and batchwise procedure.

The examples below describe the invention without restricting it thereto.

EXAMPLES

Preparation of Phenylacetic Acid

Example 1

11.6 g of a solution of 50% by weight of water [321 mmol] in N-methylpyrrolidone are added over a period of 1 hour to a solution of 36.9 g of benzyl chloride [291.5 mmol] and 26 mg of palladium chloride [0.145 mmol] in 76 g of N-methylpyrrolidone at a pressure of 30 bar of carbon monoxide with a temperature of 150° C. in a 300 ml HC4 autoclave. The pressure is kept constant during the addition at 30 bar. After approximately 10 hours of post-stirring, the carbon monoxide uptake is ended. After cooling, a GC yield of 87% phenylacetic acid is obtained. After fractional distillation, 32.1 g of phenylacetic acid [278.7 mmol], equivalent to a practical yield of 81%, are obtained. The melting point is 78° C.

The low-boiler fraction contains N-methylpyrrolidone and unreacted benzyl chloride.

Example 2

10 g of a solution of 4.9 g of water (273.8 mmol) in 5 g of N-methylpyrrolidone are added over a period of 1 hour to a solution of 35 g of o-methylbenzyl chloride [248.9 mmol] and 22 mg of palladium chloride [0.124 mmol] in 75 g of N-methylpyrrolidone at a pressure of 20 bar of carbon monoxide and at a temperature of 130° C. in a 300 ml HC4 autoclave. The pressure is kept constant during the addition at 20 bar. After the addition has ended, the mixture is heated further for 12 hours to constant pressure. It is worked up in a similar manner to example 1.

The practical yield, after distillation, is 79% of o-methylphenylacetic acid [197.5 mmol]. The melting point is 88–90° C., and the GC purity is 100%.

Example 3

A solution of 4.3 g of water [239 mmol] in 5 g of N-methylpyrrolidone is added over a period of 1 hour to a solution of 35 g of o-chlorobenzyl chloride [217.4 mmol] and 20 mg of palladium chloride [0.109 mmol] in 75 g of N-methylpyrrolidone at a pressure of 20 bar of carbon monoxide and at a temperature of 130° C. in a 300 ml HC4 autoclave. The pressure is kept constant during the addition at 20 bar.

After the addition has ended, the mixture is heated for a further 9 hours to constant pressure. It is worked up after cooling in a similar manner to example 1.

The practical yield is 82%, this is equivalent to a mass of 30.3 g of o-chlorophenylacetic acid of a GC purity of 100% and a melting point of 95–97° C.

Example 4

10 g of a solution of 5 g of water [278 mmol] and 5 g of N-methylpyrrolidone are added over a period of 1 hour to a solution of 49 g of 2,4-dichlorobenzyl chloride [252.5 mmol] and 18 mg of palladium chloride [0.1 mmol] in 105 g of N-methylpyrrolidone at a pressure of 20 bar of carbon monoxide and a temperature of 130° C. in a 300 ml HC4 autoclave. The pressure is kept constant during addition at 20 bar. The mixture is further stirred to constant pressure, which is reached after 16 hours. After cooling, the N-methylpyrrolidone and the hydrogen chloride are removed at 150° C. and 200 mbar. The residue is added as a melt to water with parallel addition of 50% strength aqueous sodium hydroxide solution, so that a pH of 10 is maintained. A homogeneous solution is obtained, which is extracted with 20 ml of xylene to remove substances soluble in organic solvents.

The mixture is then acidified to pH 1 with approximately 30% strength aqueous hydrochloric acid, the 2,4-dichlorophenylacetic acid precipitating out as white solid. The precipitated product is washed with water until the effluent wastewater has a constant pH. The washed product is dried at 100° C. and reduced pressure.

The practical yield is 89% having a GC purity of 100% of 2,4-dichlorophenylacetic acid. The melting point is 131–133° C.

What is claimed is:

1. A process for preparing phenylacetic acid derivatives of the formula (I) by reacting benzyl chlorides of the formula (II)

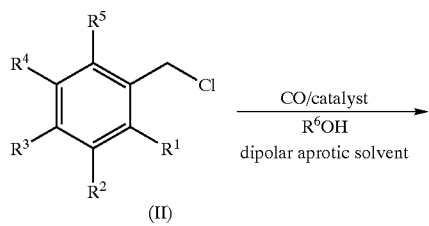

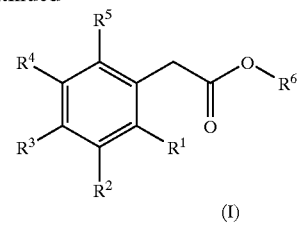

with a compound of the formula $R^6OH$ and with carbon monoxide in a dipolar aprotic solvent in the presence of a catalyst which comprises at least one element of compound of a transition metal of subgroup VIII of the Periodic Table of the Elements, where $R^1$, $R^2$, $R^3$, $R^4$, and $R^5$ independently of one another are the following radicals:

a hydrogen or fluorine atom;

a $CH_2Cl$ radical;

a $HO_2CCH=CH-$, $NC-$ or $CF_3-$ group;

an alkyl, alkoxy or acyloxy radical having in each case 1 to 18 carbon atoms; or a $C_6$–$C_{18}$-aryloxy, aryl or heteroaryl radical, where, as heteroatoms, 1 to 3 atoms selected from the group consisting of O, N and/or S are present; a $R^8{}_2P(=O)-$, $R^9C(=O)-$, $R^9OC(=O)-$, $R^9OC(=O)CH=CH-$, $R^{10}C(=O)-$, $R^{10}OC(=O)-$, $R^{10}OC(-O)CH=CH-$, or $R^{10}{}_2P(=O)-$ radical, where $R^8$ is a $C_1$–$C_4$-alkyl radical, $R^9$ is a $C_1$–$C_{18}$-alkyl radical or hydrogen and $R^{10}$ is a $C_6$–$C_{18}$-aryl radical; or where at least two of the radicals $R^1$, $R^2$, $R^3$, $R^4$, and $R^5$ are linked to one another and form at least one aliphatic or aromatic ring having 5 to 18 carbon atoms; $R^6$ is hydrogen or a $C_1$–$C_{18}$-alkyl or $C_6$–$C_{18}$-aryl radical;

where said catalyst is selected from the group of: palladium, palladium compounds; palladium compounds comprising nickel and/or cobalt; and where the reaction is carried on in the presence of an ionic halide.

2. The process as claimed in claim 1, wherein $R^1$, $R^2$, $R^3$, $R^4$, and $R^5$ independently of one another hydrogen, fluorine, a $C_1$–$C_8$-alkyl or a $C_1$–$C_8$-alkoxy radical, or two of the radicals $R^1$, $R^2$, $R^3$, $R^4$, and $R^5$ are linked to one another and form an aliphatic or aromatic ring having 5 to 10 carbon atoms.

3. The process as claimed in claim 1, wherein $R^6$ is a $C_1$–$C_4$-alkyl radical or hydrogen.

4. The process as claimed in claim 1, wherein the ionic halide is an alkali metal halide or an ammonium halide or an alkylammonium halide or a phosphonium halide.

5. The process as claimed in claim 1, wherein the catalyst additionally contains a ligand.

6. The process as claimed in claim 5, wherein the ligand is a phosphine compound.

7. The process as claimed in claim 1, wherein the catalyst is used in an amount of 0.00001 to 0.3 mol of transition metal per mole of benzyl chloride of the formula (II).

8. The process as claimed in claim 1, wherein the reaction is carried out at a CO pressure of 0.5 to 20 MPa.

9. The process as claimed in claim 1, wherein the reaction is carried out at a temperature in the range from 20 to 220° C.

10. A process for preparing phenylacetic acid derivatives of the formula (I) consisting essentially of:

reacting benzyl chlorides of the formula (II)

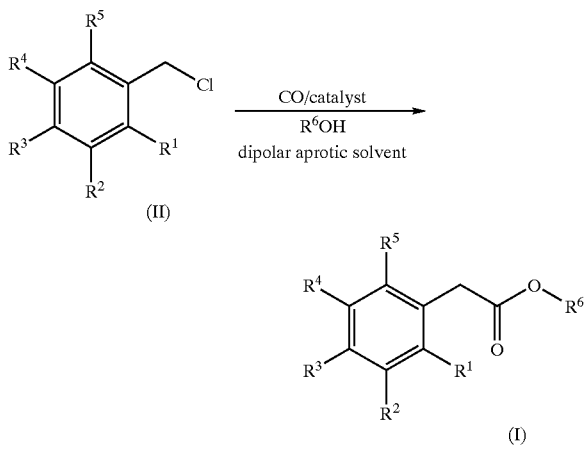

with a compound of the formula R⁶OH and with carbon monoxide in a dipolar aprotic solvent in the presence of a catalyst which consists essentially of at least one element or compound of a transition metal of subgroup VIII of Periodic Table of the Elements, where $R^1$, $R^2$, $R^3$, $R^4$, and $R^5$ independently of one another are the following radicals:
a hydrogen or fluorine atom;
a $CH_2Cl$ radial;
a $HO_2CCH=CH-$, $NC-$ or $CF_3-$ group;
an alkyl, alkoxy or acyloxy radical having in each cast 1 to 18 carbon atoms; or a $C_6-C_{18}$-aryloxy, aryl or heteroaryl radical, where, as heteroatoms, 1 to 3 atoms selected from the group consisting of O, N and/or S are present: a $R^8{}_2P(=O)-$, $R^9C(=O)-$, $R^9OC(=O)-$, $R^9OC(=O)CH=CH-$, $R^{10}C(=O)-$, $R^{10}OC(=O)-$, $R^{10}OC(=O)CH-$, or $R^{10}{}_2P(=O)-$ radical, where $R^8$ is a $C_1-C_4$-alkyl radical, $R^9$ is a $C_1-C_{18}$-alkyl radical or hydrogen and $R^{10}$ is a $C_6-C_{18}$-aryl radical; or where at least two of the radicals $R^1$, $R^2$, $R^3$, $R^4$, and $R^5$ are linked to one another and form at least one aliphatic or aromatic ring having 5 to 18 carbon atoms; $R^6$ is hydrogen or a $C_1-C_{18}$-Alkyl or $C_6-C_{18}$-aryl radical;
where said catalyst is selected from the group of: palladium, palladium compounds, palladium compounds comprising nickel and/or cobalt;
where said catalyst additionally contains a ligand, said ligand being a phosphine compound; and
where the reaction is carried out in the presence of an ionic halide, said ionic halide is an alkali metal halide or an ammonium halide or an alkylammonium halide or a phosphonium halide.

11. The process as claimed in claim 10, wherein $R^1$, $R^2$, $R^3$, $R^4$, and $R^5$ independently of one another are hydrogen, fluorine, a $C_1-C_8$-alkyl or a $C_1-C_8$-alkoxy radical, or two of the radicals $R^1$, $R^2$, $R^3$, $R^4$, and $R^5$ are linked to one another and form an aliphatic or aromatic ring having 5 to 10 carbon atoms.

12. The process as claimed in claim 10, wherein $R^6$ is a $C_1-C_4$-alkyl radical or hydrogen.

13. The process as claimed in claim 10, wherein the catalyst is used in an amount of 0.00001 to 0.3 mol of transition metal per mole of benzyl chloride of the formula (II).

14. The process as claimed in claim 10, wherein the reaction is carried out at a CO pressure of 0.5 to 20 MPa.

15. The process as claimed in claim 10, wherein the reaction is carried out at a temperature in the range from 20 to 220° C.

16. A process for preparing phenylacetic acid derivatives of the formula (I) by reacting benzyl chlorides of the formula (II)

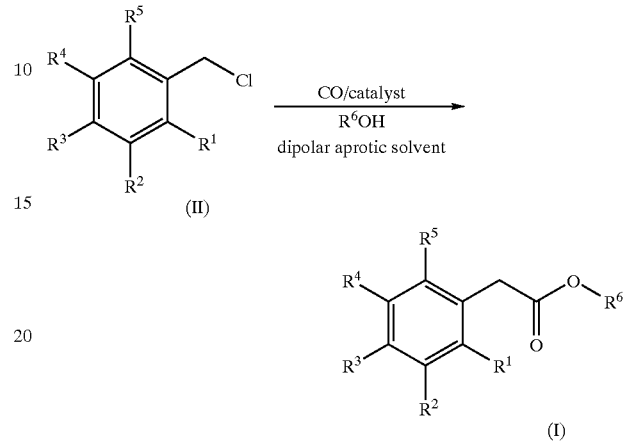

with a compound of the formula R⁶OH and with carbon monoxide in a dipolar aprotic solvent in the presence of a catalyst which comprises at least one element or compound of a transition metal of subgroup VIII of the Periodic Table of the Elements, where $R^1$, $R^2$, $R^3$, $R^4$, and $R^5$ independently of one another are the following radicals:
a hydrogen or fluorine atom;
a $CH_2Cl$ radical;
a $HO_2CCH=CH-$, $NC-$ or $CF_3-$ group;
an alkyl, alkoxy or acyloxy radical having in each case 1 to 18 carbon atoms; or a $C_6-C_{18}$-aryloxy, aryl or heteroaryl radical, where, as heteroatoms, 1 to 3 atoms selected from the group consisting of O, N and/or S are present; a $R^8{}_2P(=O)-$, $R^9C(=O)-$, $R^9OC(=O)-$, $R^9OC(=O)CH-CH-$, $R^{10}C(=O)-$, $R^{10}OC(=O)-$, $R^{10}OC(=O)CH=CH-$, or $R^{10}{}_2P(=O)-$ radical, where $R^8$ is a $C_1-C_4$-alkyl radical, $R^9$ is a $C_1-C_{18}$-alkyl radical or hydrogen and $R^{10}$ is a $C_6-C_{18}$-aryl radical; or where at least two of the radicals $R^1$, $R^2$, $R^3$, $R^4$, and $R^5$ are linked to one another and form at least one aliphatic or aromatic ring having 5 to 18 carbon atoms; $R^6$ is hydrogen or a $C_1-C_{18}$-alkyl or $C_6-C_{18}$-aryl radical;
where said catalyst is selected from the group of: palladium, palladium compounds, palladium compounds comprising nickel and/or cobalt;
where said catalyst is used in an amount of 0.00001 to 0.3 mol of transition metal per mole of benzyl chloride of the formula (II);
where said catalyst additionally contains a ligand, said ligand being a phosphine compound;
where the reaction is carried out in the presence of an ionic halide, said ionic halide is an alkali metal halide or an ammonium halide or an alkylammonium halide or a phosphonium halide;
where the reaction is carried out at a CO pressure of 0.5 to 20 MPa; and
where the reaction is carried out at a temperature in the range from 20 to 220° C.

* * * * *